United States Patent [19]

Schaub et al.

[11] Patent Number: 4,609,668
[45] Date of Patent: Sep. 2, 1986

[54] FUNGICIDAL α-(ALKYNYLPHENYL)AZOLE ETHANOL COMPOUNDS

[75] Inventors: Fritz Schaub, Aesch; Rupert Schneider, Riehen, both of Switzerland

[73] Assignee: Sandoz Ltd., Basel, Switzerland

[21] Appl. No.: 644,401

[22] Filed: Aug. 24, 1984

[30] Foreign Application Priority Data

Sep. 1, 1983 [GB] United Kingdom ............... 8323412
Apr. 4, 1984 [GB] United Kingdom ............... 8408655

[51] Int. Cl.$^4$ ............... A01N 43/50; A01N 43/653; C07D 233/60; C07D 249/08
[52] U.S. Cl. ............... 514/383; 514/184; 514/399; 548/101; 548/262; 548/341; 549/512; 549/551; 549/554; 549/563; 556/436; 568/308; 568/331; 568/332; 568/333; 568/335; 568/337; 570/185
[58] Field of Search ............... 548/101, 262, 341; 514/184, 399, 383

[56] References Cited

U.S. PATENT DOCUMENTS

| | | | |
|---|---|---|---|
| 3,826,836 | 7/1974 | Buchel et al. | 548/341 |
| 4,147,793 | 4/1979 | Shephard et al. | 548/341 |
| 4,414,210 | 11/1983 | Miller et al. | 514/383 |

FOREIGN PATENT DOCUMENTS

| | | | |
|---|---|---|---|
| 2063260 | 6/1981 | United Kingdom | 548/341 |
| 2064520 | 6/1981 | United Kingdom | 548/262 |

*Primary Examiner*—Alton D. Rollins
*Attorney, Agent, or Firm*—Hana Dolezalova; Jacqueline S. Larson

[57] ABSTRACT

The invention provides novel α-(ethynyl substituted phenyl)-α-hydrocarbyl-1H-azole-ethanols wherein the azole group is 1,2,4-triazol-1-yl or imidazol-1-yl, the ethynyl group is unsubstituted or substituted and the phenyl group may bear an additional substituent and ethers thereof, which are useful as fungicides.

29 Claims, No Drawings

FUNGICIDAL α-(ALKYNYLPHENYL)AZOLE ETHANOL COMPOUNDS

The present invention relates to novel α-aryl-1H-azole-1-ethanols, their use, compositions for facilitating their use and the preparation of novel compounds of the invention.

The present invention provides α-(ethynyl substituted phenyl)-α-hydrocarbyl-1H-azole-1-ethanols wherein the azole group is 1,2,4-triazol-1-yl or imidazol-1-yl, the ethynyl group is unsubstituted or substituted and the phenyl group may bear an additional substituent (e.g. by the substituents indicated for the compounds of formula I hereinafter), and ethers of such ethanol compounds.

The term hydrocarbyl as used herein is intended to embrace any hydrocarbyl whether saturated or unsaturated, whether straight or branched or partially or completely in ring form, whether aliphatic or aromatic, unsubstituted or substituted; where the hydrocarbyl is aliphatic or cycloaliphatic it contains conveniently up to 8 carbon atoms, where it contains an aromatic or cycloaliphatic group it contains conveniently up to 9 carbon atoms. Suitable substituents of aliphatic or cycloaliphatic moieties of the hydrocarbyl group are e.g. halogen. Suitable substituents of aromatic moieties of the hydrocarbyl group are i.a. halogen, $C_{1-5}$alkoxy $C_{1-5}$alkyl, $C_6H_5$, $CF_3$, $OCF_3$ and $NO_2$.

A suitable subgroup of compounds of the invention is of formula I

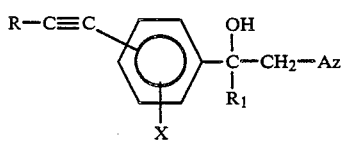   I wherein

R is H, halogen; $C_{1-5}$alkyl; $C_{2-5}$alkenyl; $C_{3-7}$cycloalkyl; phenyl or phenyl-$C_{1-3}$alkylene, unsubstituted or substituted in the phenyl ring, $R_1$ is $C_{1-8}$alkyl, $C_{2-8}$alkenyl or $C_{2-8}$alkinyl unsubstituted or substituted by halogen; or is $C_{3-6}$cycloalkyl or $C_{3-6}$-cycloalkyl-$C_{1-3}$alkylene unsubstituted or substituted by $C_{1-3}$alkyl or $C_{3-6}$cycloalkyl; or is phenyl or phenyl-$C_{1-3}$alkylene unsubstituted or substituted in the phenyl ring, Az is 1,2,4-triazole-1-yl or imidazole-1-yl, and X is H, $C_{1-5}$alkyl, $C_{1-5}$alkoxy, halogen, $CF_3$, $OCF_3$, $NO_2$ or phenyl, and ethers thereof.

The compounds of the invention contain one or more chiral centers. Such compounds are generally obtained in the form of racemic or diastereomeric mixtures. However, these and other mixtures can if desired be separated either completely or partly into the individual isomers or desired isomer mixtures by methods known in the art.

Where R is halogen, this is for example Cl, Br or I.

Where R and/or $R_1$ is phenyl or phenyl-$C_{1-3}$alkylene substituted in the phenyl ring, such substituents are for example halogen (e.g. F, Cl, Br, I), $C_{1-5}$alkyl (e.g. $CH_3$) or $C_{1-5}$alkoxy (e.g. $CH_3O$), $CF_3$, $OCF_3$, $NO_2$ or phenyl.

Where R and/or $R_1$ contain a $C_{1-3}$alkylene group, such alkylene group is for example $CH_2$ or $CH(CH_3)$.

Where $R_1$ is $C_{1-8}$alkyl it is preferably $iC_3H_7$ or $tC_4H_9$.

Where $R_1$ is halogen substituted $C_{1-8}$alkyl, $C_{2-8}$alkenyl or $C_{2-8}$alkinyl, the halogen substituent may be F, Cl, Br or I.

Where $R_1$ is or contains $C_{3-6}$cycloalkyl, such cycloalkyl is preferably cyclopropyl.

The ethynyl substituent is conveniently in m- or p-position of the phenyl group, preferably in para.

Where the ethanol hydroxy group of the compounds of the invention is etherified, such ethers are e.g. $C_{1-5}$alkyl such as methyl ethers.

The compounds of the invention are obtained by reaction of an 2-(ethynyl substituted phenyl)-2-hydrocarbyl-oxirane, wherein the ethynyl group may be substituted and the phenyl group may bear an additional substituent or a reactive functional derivative of such oxirane, with 1,2,4-triazol or imidazole, followed where desired by the substitution of the ethynyl, if this is unsubstituted, by halogen, and/or by etherification of the thus obtained ethanol compound.

The compounds of formula I are accordingly obtained by the following processes comprising (a) reacting an oxirane of formula II

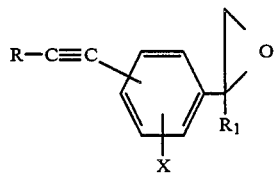   II wherein R, $R_1$ and X are as defined above, or a reactive functional derivative thereof, with 1,2,4-triazole or imidazole, followed, where desired, by etherification of the thus obtained ethanol compound, or (b) obtaining a compound of formula Ib

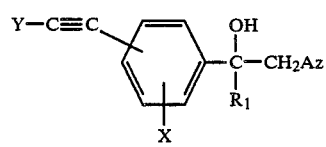   Ib wherein $R_1$, X and Az are as defined above, and Y is halogen, by substitution of the ethynyl hydrogen in a compound of formula Ic

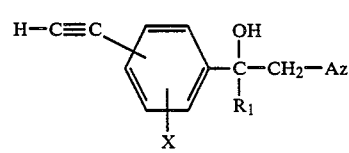   Ic wherein $R_1$, X and Az are as defined above, by Y (halogen), followed, where desired, by etherification of the thus obtained ethanol compound.

Process (a) is a reaction known per se for the preparation of azole-1-ethanols by reaction of an oxirane with an azole. The reaction can be effected under conditions analogous to that of such known reactions; it is advantageous to use the azole in salt form (e.g. as alkalimetal salt such as Na or K salt), in trialkylsilyl form (e.g. trimethylsilyl form) or to effect the reaction in the presence of an acid binding agent.

The reaction with the oxirane according to process (a) is conveniently effected in a solvent which is inert under the reaction conditions, e.g. in dimethylformamide. A suitable reaction temperature is between ambient temperature and reflux temperature of the reaction mixture; where the azole is in trialkylsilyl form it is conveniently higher than ambient temperature, e.g. between 70° and 90° C. Where a trialkylsilyl azole is reacted, the reaction is conveniently effected in the presence of a base such as NaH.

The term "reactive functional derivative" used in connection with the above 2-aryl-2-$R_1$-oxiranes, such as the compounds of formula II, is intended to embrace any oxirane derivative that, by reaction with an azole results in ethanol compounds of the invention. Various examples of such reactive derivatives are known to a person skilled in the art; a suitable example thereof are the corresponding halohydrines (wherein the halogen is e.g. Cl or Br).

The conditions at which the azoles may be reacted with the reactive functional derivatives of the above defined 2-aryl-2-$R_1$-oxiranes are also known per se. The reaction of an azole with the halohydrine derivative of a compound of formula II, can be effected under the conditions dislosed for the reaction with the oxirane compounds, conveniently, however, in the presence of an additional equivalent of a base.

The substitution of the ethynyl hydrogen in compounds of formula Ic by halogen is also effected according to processes known per se for such type of substitution reaction. It may be effected either directly, by reaction of a compound of formula Ic with a halogen cation donor such as an alkalimetal hypohalogenite (e.g. Na- or KClO), N-Cl- or N-Br-succinimide or $CCl_4$ (the latter under strong alkaline conditions), or via the di-Y addition product followed by the splitting off of HY from the addition product.

Ether derivatives of the ethanol compounds of the invention may be obtained according to known etherification procedures starting from the corresponding ethanols. Suitable O-alkylation agents are for example the corresponding halides, e.g. iodides such as methyl iodide.

The compounds of the invention are isolated from the reaction mixture in which they are formed by established procedures. They are obtained in free form or in salt or metal complex form, e.g. as acid addition salt with an organic or inorganic acid such as hydrochloride, or as alcoholate e.g. as Na ethanolate, or in metal complex form, e.g. with a metal such as copper and zinc, and with anions such as chloride, sulphate and nitrate.

The oxiranes of formula II are novel. They are obtained from the corresponding compounds of formula IV

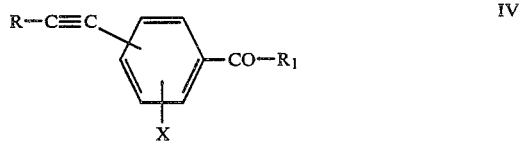

wherein R', X and $R_1$ are as defined above, by reaction with the dimethyl sulfonium-methylide, dimethyl oxosulfonium-methylide, a $C_{8-12}$alkyl methyl sulfonium-methylide or a polymer bound (e.g. polystyryl) methyl sulfonium-methylide (see Tetrahedron Letters 3, pp. 203–206 (1979).

The compounds of formula IV are obtained according to methods known per se.

Compounds of formula IVa

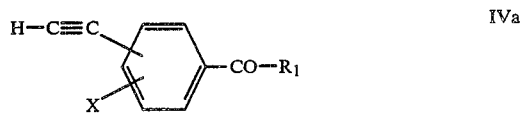

wherein $R_1$ and X are as defined above, may for example be prepared by reaction of a compound of formula V

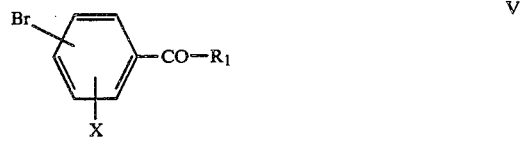

wherein $R_1$ and X are as defined above, with trimethylsilylacetylene in the presence of catalytic amounts of bis[triphenylphosphine]palladium dichloride and copper(I) iodide in amines such as diethylamine or piperidine and subsequent removal of the silyl group e.g. by mild treatment with dilute aqueous KOH in methanol (see Synthesis 1980(8) p. 627). The trimethylsilylacetylene used in this reaction may be replaced by 2-methyl-3-butyn-2-ol, whereby the same Pd catalyst and CuI Promotor is used; the compounds of formula IV are then obtained by treatment of the reaction product with NaOH in toluene (see U.S. Pat. No. 4,223,172).

Compounds of formula IVb

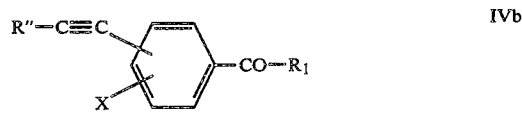

wherein
$R_1$ and X are as defined above and
R" is $C_{1-5}$alkyl; $C_{2-5}$alkenyl; phenyl or phenyl-$C_{1-3}$alkylene unsubstituted or substituted in the phenyl ring, are obtained by reaction of a compound of formula V with a compound of formula VI

   VI wherein R" is as defined above.

The reaction conditions are analogous to those specified for the reaction of a compound of formula V with trimethylsilylacetylene.

Depending on the meaning of $R_1$ it may be advantageous to prepare compounds of formula IV starting from compounds of formula VII

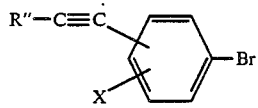   VII wherein X and R" are as defined above, under the conditions known for a Grignard synthesis of ketones.

Insofar as the production of any starting material is not particularly described, these compounds are known, or may be produced and purified in accordance with known processes, or in a manner analogous to processes described herein to or known processes.

The compounds of the invention in free form or in agriculturally acceptable salt or complex form are useful as fungicides in the combatting of phytopathogenic fungi. Their advantageous fungicidal activity is established by in vivo tests with test concentrations of from about 0.0008 to 0.05% against *Uromyces appendiculatus* (bean rust) or pole beans, against other rust fungi (such as Hemileia, Puccinia) on coffee, wheat, pelargonium, snapdragon, against *Erysiphe cichoracearum* on cucumber and against other powdery mildew fungi (*E. graminis* f.sp. *tritici, E. graminis* f.sp. *hordei, Podosphaera leucotricha, Uncinula necator*) on wheat, barley, apple, grapevine. Further interesting activities are i.a. observed in vitro against *Ustilago maydis* and in vivo against *Rhizoctonia solani*. Many of the compounds of the invention have an excellent plant tolerance and a good systemic action. The compounds of the invention are therefore indicated for treatment of plant, seeds and soil to combat phytopathogenic fungi, e.g. Basidiomycetes of the order Uredinales (rusts) such as Puccinia spp, Hemileia spp, Uromyces spp; Ascomycetes of the order Erysiphales (powdery mildew) such as Erysiphe spp, Podosphaera spp, and Uncinula spp, and of the oder Pleosporales such as Venturia spp; as well as Phoma, Rhizoctonia, Helminthosporium, Pyricularia, Pellicularia (=Corticium), Thielaviopsis and Stereum spp.

The amount of compound of the invention to be applied, will depend on various factors such as the compound employed, the subject of the treatment (plant, soil, seed), the type of treatment (e.g. drenching, sprinkling, spraying, dusting, dressing), the purpose of the treatment (prophalactic or therapeutic), the type of fungi to be treated and the application time.

In general, satisfactory results are obtained, if the compounds of the invention are applied in an amount of from about 0.005 to 2.0, preferably about 0.01 to 1 kg/ha, in the case of a plant or soil treatment; e.g. 0.04 to 0.125 kg of active ingredient (a.i.) per ha in crops such as cereals, or concentrations of 1 to 5 g of a.i. per ha in crops such aas fruits, vineyards and vegetables (at an application volume of from 300 to 1000 l/ha—depending on the size or leaf volume of the crop—which is equivalent to an application rate of approximately 10–50 g/ha). The treatment can, if desired, be repeated, e.g. at intervals of 8 to 30 days.

Where the compounds of the invention are used for seed treatment, satisfactory results are in general obtained, if the compounds are used in an amount of from about 0.05 to 0.5, preferably about 0.1 to 0.3 g/kg seeds.

The term soil as used herein is intended to embrace any conventional growing medium, whether natural or artificial.

The compounds of the invention may be used in a great number of crops, such as soybean, coffee, ornamentals (i.a. pelargonium, roses), vegetables (e.g. peas, cucumber, celery, tomato and bean plants), sugarbeet, sugarcane, cotton, flax, maize (corn), vineyards, pomes and stone fruits (e.g. apple, pears, prunes) and in cereals (e.g. wheat, oats, barley, rice).

In view of their good crop tolerance many of the compounds of the invention are particularly indicated for fungicidal treatments where a favourable crop tolerance is desirable or essential, e.g. in fruit crops such as apples. Various compounds of the invention, e.g. the compound of example 2.33 hereinafter, possess also a favourable curative activity.

Particularly favourable results are i.a. obtained with compounds of formula I having one or more of the following features.

X is H, the group C≡CR is in the para-position,

R is H, Cl, Br, $CH_3$, $C_4H_9$ (e.g. n-$C_4H_9$ or t-$C_4H_9$) or phenyl (unsubstituted or substituted), particularly Br or unsubstituted phenyl, preferably the latter, $R_1$ is i$C_3H_7$, t$C_4H_9$, $C_{3-6}$cycloalkyl (particularly cyclopropyl) or $C_{3-6}$cycloalkyl-$C_{1-3}$alkylene, particularly cyclopropyl-$C_{1-3}$alkylene, preferably cyclopropyl-CH(CH$_3$), Az is 1,2,4-triazol-1yl.

The invention also provides fungicidal compositions, comprising as a fungicide a compound of the invention in free form, or in fungicidally acceptable salt or complex form in association with a fungicidally acceptable diluent (hereinafter diluent). They are obtained in conventional manner, e.g. by mixing a compound of the invention with a diluent and optionally additional ingredients, such as surfactants.

The term diluents as used herein means liquid or solid, fungicidally acceptable material, which may be added to the active agent to bring it in an easier or better applicable form, resp. to dilute the active agent to a usable or desirable strength of activity. Examples of such diluents are talc, kaolin, diatomaceous earth, xylene or water.

Especially formulations used in spray form, such as water dispersable concentrates or wettable powders, may contain surfactants such as wetting and dispersing agents, e.g. the condensation product of formaldehyde with naphthalene sulphonate, an alkylarylsulphonate, a lignin sulphonate, a fatty alkyl sulphate, an ethoxylated alkylphenol and an ethoxylated fatty alcohol.

In general, the formulations include from 0.01 to 90% by weight of active agent, from 0 to 20% fungicidally acceptable surfactant and from 10 to 99.99% diluent(s). Concentrated forms of composition, e.g. emulsion concentrates, contain in general from about 2 to 90%, preferable from between 5 and 70% by weight of active agent. Application forms of formulation contain in general from 0.0005 to 10% by weight of a compound of the invention as active agent. Typical spray-suspensions may, for example, contain 0.0005 to 0.05, preferably 0.001 to 0.02% e.g. 0.001, 0.002 or 0.005% by weight of active agent.

In addition to the usual diluents and surfactants, the compositions of the invention may comprise further additives with special purposes, e.g. stabilizers, desactivators (for solid formulations or carriers with an active surface), agents for improving the adhesion to plants, corrosion inhibitors, anti-foaming agents and colorants. Moreover, further fungicides with similar or complementary fungicidal activity, e.g. sulphur, chlorothalonil, dithiocarbamates such as mancozeb, maneb, zineb, propineb, trichloromethane-sulphenylphthalimides and analoges such as captan, captafol and folpet, benzimidazoles such as benomyl, or other beneficially-acting materials, such as insecticides may be present in the formulations.

Examples of plant fungicide formulations are as follows:

a. Wettable Powder Formulation

10 Parts of a compound of the invention are mixed and milled with 4 parts of synthetic fine silica, 3 parts of sodium lauryl sulphate, 7 parts of sodium lignin sulphonate and 66 parts of finely divided kaolin and 10 parts of diatomaceous earth until the mean particle size is about 5 micron. The resulting wettable powder is diluted with water before use to a spray liquor which may be applied by foliar spray as well as by root drench application.

b. Granules

Onto 94.5 parts by weight of quartz sand in a tumbler mixer are sprayed 0.5 parts by weight of a binder (non-ionic tenside) and the whole thoroughly mixed. 5 Parts by weight of a compound of the invention are then added and thorough mixing continued to obtain a granulate formulation with a particle size in the range of from 0.3 to 0.7 mm. The granules may be applied by incorporation into the soil adjacent to the plants to be treated.

c. Emulsion Concentrate

25 Parts by weight of a compound of the invention are mixed with 10 parts by weight of an emulsifier and 65 parts by weight of xylene. The concentrate is diluted with water to the desired concentration.

d. Seed Dressing 45 parts of a compound of the invention are mixed with 1.5 parts of diamyl phenoldecaglycolether ethylene oxide adduct, 2 parts of spindle oil, 51 parts of fine talcum and 0.5 parts of colorant rhodanin B. The mixture is ground in a contraplex mill at 10,000 rpm until an average particle size of less than 20 microns is obtained. The resulting dry powder has good adherance and may be applied to seeds, e.g. by mixing for 2 to 5 minutes in a slowly turning vessel.

The following examples further illustrate the present invention. All temperatures are in centigrade. Rf values are on silica-gel (TLC).

FINAL COMPOUNDS

EXAMPLE 1

2-(4-Ethynylphenyl)-3,3-dimethyl-1-(1H-1,2,4-triazol-1-yl)butan-2-ol 17.2 g Dodecyldimethylsulfoniummethylsulfate are added, at room temperature, to a solution of 6.5 g 1-(4-ethinylphenyl)-2,2-dimethylpropan-1-one in 80 ml absolute toluene. The mixture is stirred during 15 minutes, then 3.8 g pulverised KOH are added and the mixture stirred further during 22 hours at 35°. The reaction mixture is poured onto ice, adjusted to pH 7 with 6N $H_2SO_4$ and extracted with diethylether. The organic phase is washed with water, dried (with $Na_2SO_4$) and evaporated in vacuum. The residue, containing 2-(4-ethynylphenyl)-2-(1,1-dimethylethyl)-oxirane is reacted further, without purification.

The residue is added dropwise during 10 minutes and at 90°, to a suspension of 4 g 1,2,4-triazole and 14.5 g $K_2CO_3$ in 80 ml absolute dimethylformamide and stirred during 4 hours at 90°. The reaction mixture is then cooled, poured onto ice and extracted with diethylether. The etheric solution is washed with water, dried and concentrated in vacuum. The residue is stirred with hexane, the insoluble solid product filtered off and recrystallised from hexane/toluene. The title compound is obtained in the form of colourless crystals, m.p. 101° (Rf=0.35 ethylacetate/hexane 6:4).

EXAMPLE 2

Analogous to the procedure of Example 1, the following compounds of formula I wherein X=H and where the R—C≡C—group is in the para-position, if not otherwise indicated, are obtained (starting from the corresponding ketones of formula IV, via the corresponding oxiranes of formula II).

TABLE I

| Example | R | $R_1$ | Az | Rf, m.p. |
|---|---|---|---|---|
| 2.1 | H | i-$C_3H_7$ | Tr[1] | 121° |
| 2.2 | $CH_3$ | i-$C_3H_7$ | Tr | 98–99° |
| 2.3 | $CH_3$ | i-$C_3H_7$ | Im[2] | 180° |
| 2.4 | $C_6H_5$ | i-$C_3H_7$ | Tr | 71° |
| 2.5 | $C_6H_5$ | i-$C_3H_7$ | Im | 188° |
| 2.6 | $C_6H_5$ | t-$C_4H_9$ | Tr | Rf = 0.35[3] |
| 2.7 | $C_6H_5$ | t-$C_4H_9$ | Im | Rf = 0.35[4] |
| 2.8 | $CH_3$ | t-$C_4H_9$ | Tr | 99° |
| 2.9 | $CH_3$ | t-$C_4H_9$ | Im | |

TABLE I-continued

| Example | R | $R_1$ | Az | Rf, m.p. |
|---|---|---|---|---|
| 2.10 | n-$C_4H_9$ | t-$C_4H_9$ | Tr | 77–78° |
| 2.11 | n-$C_4H_9$ | t-$C_4H_9$ | Im | |
| 2.12 | n-$C_4H_9$ | i-$C_3H_7$ | Tr | 65° |
| 2.13 | n-$C_4H_9$ | i-$C_3H_7$ | Im | |
| 2.14 | 4-Cl—$C_6H_4$ | t-$C_4H_9$ | Tr | 125–127° |
| 2.15 | 4-Cl—$C_6H_4$ | t-$C_4H_9$ | Im | 158° |
| 2.16 | 4-F—$C_6H_4$ | i-$C_3H_7$ | Tr | 150° |
| 2.17 | 4-F—$C_6H_4$ | i-$C_3H_7$ | Im | |
| 2.18 | 4-$CH_3O$—$C_6H_4$ | i-$C_3H_7$ | Tr | 132–133° |
| 2.19 | 4-$CH_3O$—$C_6H_4$ | i-$C_3H_7$ | Im | 175–176° |
| 2.20 | 4-$CH_3O$—$C_6H_4$ | t-$C_4H_9$ | Tr | 140° |
| 2.21 | 4-$CH_3O$—$C_6H_4$ | t-$C_4H_9$ | Im | 142–143° |
| 2.22 | 4-Cl—$C_6H_4$ | i-$C_3H_7$ | Tr | 129° |
| 2.23 | $C_6H_5$ | $CH_2$—$CH(CH_3)_2$ | Tr | 119° |
| 2.24 | $C_6H_5$ | $CH(CH_3)$—$CH(CH_3)_2$ | Tr | 97° |
| 2.25 | $C_6H_5$ | $C(CH_3)_2$—$CH(CH_3)_2$ | Tr | |
| 2.26 | $CH_3$ | $CH_2$—$CH(CH_3)_2$ | Tr | |
| 2.27 | $CH_3$ | $CH(CH_3)$—$CH(CH_3)_2$ | Tr | 117° |
| 2.28 | $CH_3$ | $C(CH_3)_2$—$CH(CH_3)_2$ | Tr | |
| 2.29 | t-$C_4H_9$ | i-$C_3H_7$ | Tr | 198° |
| 2.30 | t-$C_4H_9$ | t-$C_4H_9$ | Tr | 268–269° |
| 2.31 | n-$C_4H_9$ | $CH_2$—$CH(CH_3)_2$ | Tr | 66° |
| 2.32 | 4-$NO_2$—$C_6H_4$ | t-$C_4H_9$ | Tr | 227° |
| 2.33 | $C_6H_5$ | $CH(CH_3)$—$C_3H_5$[(5)] | Tr | (6) |
| 2.34 | $C_6H_5$ | i-$C_3H_7$ | Tr | 83–84° (R—C≡C in m-position) |
| 2.35 | $C_6H_5$ | $CH(CH_3)$—$C_3H_5$ | Im | 139° (Diast. mixture) |
| 2.36 | 4-F—$C_6H_4$ | t-$C_4H_9$ | Tr | 122° |
| 2.37 | $C_6H_5$ | cyclopropyl | Tr | 126° |
| 2.38 | H | cyclopropyl | Tr | 88° |
| 2.39 | n$C_4H_9$ | cyclopropyl | Tr | Rf = 0.35 (ethyl acetate/hexane 6:4) |
| 2.40 | $C_6H_5$ | $C(CH_3)_2$—$CH_2$—CH=$CH_2$ | Tr | Rf = 0.45 (toluene/ethyl acetate 6:4) m.p. 84° |

[(1)] 1,2,4-triazole-1-yl
[(2)] imidazole-1-yl
[(3)] ethylacetate/hexane 6:4
[(4)] ethylacetate/ethanol 40:1
[(5)] $C_3H_5$ = cyclopropyl
[(6)] Diastereomeric mixture, separated by TLC:Diastereomere A: Rf = 0.3 (ethyl acetate/hexane 6:4)Diastereomere B: Rf = 0.4 (ethyl acetate/hexane 6:4)The latter (B-form) could be crystallised, m.p. 91–92°.

EXAMPLE 3

2-(4-Bromethynylphenyl)-3,3-dimethyl-1-(1H,1,2,4-triazole-1-yl)butan-2-ol 2 g Brom are added to 10 ml of 2.5N aqueous NaOH and thereto added dropwise during 15 minutes and with stirring, a solution of 2.7 g 2-(4-ethynyl-phenyl)-3,3-dimethyl-1-(1H-1,2,4-triazole-1-yl)butan-2-ol in 20 ml dioxane.

The reaction mixture is kept at room temperature during 3 hours, then diluted with 100 ml of water and extracted with diethylether. The etheric solution is washed with water, dried and the solvent evaporated off. The residue is recrystallised from hexane/toluene to give colourless crystals m.p. 138° (Rf=0.4 ethylacetate/hexane 6:4).

EXAMPLE 4

Analogous to the procedure of Example 3 the following compounds of formula I wherein X=H and the R—C≡C—group is in the para-position are obtained (starting from the corresponding compounds of formula Ic).

| Example | R | $R_1$ | Az | Rf, m.p. |
|---|---|---|---|---|
| 4.1** | Cl | t-$C_4H_9$ | Tr | 45–46° |
| 4.2 | Cl | i-$C_3H_7$ | Tr | |
| 4.3 | I | i-$C_3H_7$ | Tr | 112° |
| 4.4 | Br | i-$C_3H_7$ | Tr | 197° |

Tr = 1,2,4-triazole-1-yl
**contaminated with 30% of a perchloro compound

EXAMPLE 5

2-(4-Chloroethynylphenyl)-3-methyl-1-(1H-1,2,4-triazole-1-yl)butan-2-ol

To a stirred mixture of 12 g 2-(4-ethynylphenyl)-3-methyl-1-(1H-1,2,4-triazol-1-yl)-butan-2-ol in 50 ml hexamethyl phosphoric acid triamide are added portionwise, within 15 minutes, 24.8 g of N-Cl-succinimide. The reaction is slightly exothermic (the reaction temperature rises from 20° to 30°). The reaction mixture is slightly cooled while maintaining the reaction temperature at 25°-30°, with stirring, for 1 hour.

The clear yellow reaction solution is poured into 1000 ml of water and extracted with diethylether. The diethyl ether phase is washed once with water, dried and the solvent evaporated off. The oily residue is chromatographed on a silica gel column with toluene/ethylacetate 3:7 to give the impure title compound (Rf=0.35).

EXAMPLE 6

2-(4-Iodoethynylphenyl)-3-methyl-1-(1H-1,2,4-triazole-1-yl)butan-2-ol

To a solution of 5.1 g 2-(4-ethynylphenyl)-3-methyl-1-(1H-1,2,4-triazole-1-yl)butan-2-ol in 100 ml abs. $CH_3OH$ are simultaneously added, with stirring at 20°–25°, 2.6 g iodine and 10 ml 30% NaOH solution. The reaction mixture is maintained at room temperature for 24 hours, with stirring, then poured into 500 ml $H_2O$ and extracted with $CH_2Cl_2$. The organic phase is washed, dried and evaporated. The residue is stirred in hexane fraction and kept over 16 hours at rest. The precipitate is sucked off and dried to give the title compound m.p. 122° as colourless crystals.

EXAMPLE 7

2-[4-(Phenylethynyl)phenyl]-3-methyl-1-(1H-1,2,4-triazol-1-yl)-butan-2-ol methyl ether NaH (1.6 g, 80%) is stirred in 60 ml absolute dimethylformamide and then added dropwise, within 60 minutes, to a solution of Compound 2.4 (16.6 g) in 60 ml dimethylformamide at room temperature; the mixture is stirred for 30 minutes. Then methyliodide (7.4 g) is added thereto. The mixture is stirred for 15 hours at room temperature and diluted with water; the solid precipitate is sucked off, washed with water and dried to give the title compound, m.p. 181° (petrol ether; colourless crystals), Rf=0.6 ($CHCl_3/CH_3OH$ 95:5).

EXAMPLE 8

Fungicidal Use 8.1: Mildew control in wheat

Wheat infested with *Erysiphe graminis* is treated with a spray liquor comprising the compound of Example 2.4 as active ingredient (a.i.) at a concentration of 300 mg a.i./l spray liquor. A spray volume of 500 l/ha is applied. The treatment allows a significant control of the mildew infestation.

8.2: Rust control in wheat

Wheat infested with *Puccinia striiformis* (yellow rust) is treated with a spray liquor comprising the compound of Example 2.4 at a concentration of 100 mg a.i./l spray liquor. A spray volume 1000 l/ha is applied. The treatment allows a significant control of the rust infestation.

INTERMEDIATES

EXAMPLE 9

1-(4-Ethynylphenyl)-2,2-dimethylpropan-1-one 1.4 g Bis-(triphenylphosphine)-palladium dichloride and 0.19 g CuI are added, at room temperature, to a solution of 10.5 g trimethylsilylacetylene and 23.6 g 1-(4-bromophenyl)-2,2-dimethylpropan-1-one in 350 ml absolute diethylamine. The reaction mixture is stirred during 20 hours at room temperature, evaporated to dryness at the rotary evaporator and the residue extracted several times with toluene. The toluene is evaporated off and the remaining tacky oil chromatographed on a silica-gel column with hexane/toluene 2:1 as mobile phase to give 1-(4-trimethylsilylethynylphenyl)-2,2-dimethylpropan-1-one.

21.6 of that residue are stirred during 4 hours at 40° in a mixture of 100 ml of $CH_3OH$ and 80 ml aqueous 1N KOH. The $CH_3OH$ is evaporated off at the rotary evaporator. The remaining oil is dissolved in diethylether and concentration of said reaction mixture gives the title compound as a tacky oil (Rf=0.35, toluene).

EXAMPLE 10

1-[4-(1-propynyl)-phenyl]-2-methylpropan-1-one

A 3 necked round bottom flask rinsed with nitrogen and fitted with a stirrer is charged with 11.2 g Mg together with a grain of $I_2$ in 100 ml absolute tetrahydrofurane. A mixture of 20 g 1-(4-bromophenyl)-1-propyne and 5 g ethylbromide is added dropwise thereto with stirring, at such a rate that the temperature rises up to 65°. Immediately thereafter an additional amount of 70 g of 1-(4-bromophenyl)-1-propyne in 100 ml absolute tetrahydrofurane are added that a limited reflux is observed at 65°.

When the addition is complete, the reaction mixture is stirred during 4 hours at 65° and then cooled off. Then are added during 15 minutes 27.6 g isobutyronitrile and is stirred at 50° during 8 hours. The reaction mixture is poured into 500 ml of ice water, acidified with 108 g (1.1 mol) $H_2SO_4$ and heated at 80° during 1 hour. The dark oil which was formed is partitioned off and subjected to a steam distillation. The pre-distilled oily fraction is rejected; the distilled title compound is purified by crystallisation m.p. 51° (Rf=0.4 diethylether/hexane 3:97).

The compounds of the invention and their pharmacological acceptable salts also possess interesting pharmacological, particularly antimycotic properties. The antimycotic activity can be established by in vitro tests, e.g. the in vitro series dilution test on various families and species of mycetes, such as yeasts, mold fungi and dermatophtes at concentrations of about 0.05 to about 50 μg/ml and also by in vivo tests, e.g. by systemic, p.o. application of dosages of ca. 10 to 100 mg/kg body weight on the model of the vaginal candidasis of the mouse (intra-vaginal infection with *Candida albicans*).

The compounds are therefore indicated for use as pharmaceuticals, particularly as anti-mycotics. An indicated suitable daily dosage for use as an anti-mycotic is from 70 to 2000 mg.

The compounds of the invention may be used in the form of pharmaceutically acceptable acid addition salts e.g. as hydrochloride, hydrobromide, sulphate, nitrate, hydrogen fumarate and naphthaline-1,5-disulphonate.

The compounds may be admixed with conventional pharmaceutically acceptable inert carriers, and, optionally, other excipients. They may be administered in such internally administrable unit dosage forms as tablets or capsules, or alternatively be administered topically in such conventional forms as ointments or creams or parenterally.

What we claim is:

1. A compound of formula (I)

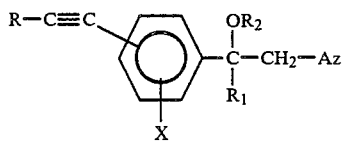 (I)

wherein
R is H, halogen; $C_{1-5}$ alkyl; $C_{2-5}$alkenyl; $C_{3-7}$cycloalkyl; phenyl or phenyl$C_{1-3}$alkylene, optionally substituted in the phenyl ring by halogen, $C_{1-5}$alkyl, $C_{1-5}$alkoxy, $CF_3$, $OCF_3$, $NO_2$ or phenyl;

$R_1$ is $C_{1-8}$alkyl, $C_{2-8}$alkenyl or $C_{2-8}$alkynyl optionally substituted by halogen; $C_{3-6}$cycloalkyl; $C_{3-6}$cycloalkyl-$C_{1-3}$alkylene optionally substituted by $C_{1-3}$alkyl or $C_{3-6}$cycloalkyl; phenyl or phenyl $C_{1-3}$alkylene optionally substituted in the phenyl ring by halogen, $C_{1-5}$alkyl, $C_{1-5}$alkoxy, $CF_3$, $OCF_3$, $NO_2$ or phenyl;

$R_2$ is H or $C_{1-5}$alkyl;

Az is 1,2,4-triazol-1-yl or imidazol-1-yl; and

X is H, $C_{1-5}$alkyl, $C_{1-5}$ alkoxy, halogen, $CF_3$, $OCF_3$, $NO_2$ or phenyl;

either in free form or in the form of acid addition salt, alcoholate or metal complex.

2. A compound of claim 1, wherein R is halogen, phenyl or phenyl-$C_{1-3}$alkylene, optionally substituted in the phenyl ring by halogen, $C_{1-5}$alkyl, $C_{1-5}$alkoxy, $CF_3$, $OCF_3$, $NO_2$ or phenyl.

3. A compound of claim 2, wherein the group R—C≡C is in the para-position and Az is 1,2,4-triazol-1-yl.

4. A compound of claim 3, wherein X is H.

5. A compound of claim 4, wherein $R_1$ is i-$C_3H_7$, t-$C_4H_9$, $C_{3-6}$cycloalkyl or $C_{3-6}$cycloalkyl-$C_{1-3}$alkylene.

6. A compound of claim 5, wherein R is phenyl.

7. A compound of claim 6, wherein $R_2$ is $C_{1-5}$alkyl.

8. A compound of claim 6, wherein $R_2$ is H.

9. The compound of claim 8, wherein $R_1$ is

cyclopropyl-CH—($CH_3$).

10. The compound of claim 8, wherein $R_1$ is isopropyl.

11. The compound of claim 8, wherein $R_1$ is cyclopropyl.

12. The compound of claim 5, wherein R is bromine, $R_1$ is t-butyl and $R_2$ is hydrogen.

13. A fungicidal composition comprising as active ingredient a fungicidally effective amount of a compound of claim 1, in free form or in the form of agriculturally acceptable acid addition salt, alcoholate or metal complex in admixture with an agriculturally acceptable diluent.

14. A fungicidal composition comprising as active ingredient compound of claim 1 in amount from 0.01 to 90% by weight, the active ingredient being in its free form or in agriculturally acceptable acid addition salt, alcoholate or metal complex form in admixture with an agriculturally acceptable diluent.

15. The composition of claim 14, in which the group R—C≡C— is in the para-position;
R is chlorine, bromine or phenyl optionally substituted by halogen, $C_{1-5}$alkyl, $C_{1-5}$alkoxy, $CF_3$, $OCF_3$, $NO_2$ or phenyl,
$R_1$ is i-$C_3H_7$, t-$C_4H_9$, $C_{3-6}$cycloalkyl or $C_{3-6}$cycloalkyl-$C_{1-3}$alkylene;
X is hydrogen; and
Az is 1,2,4-triazole-1-yl.

16. The composition of claim 15, in which R is phenyl.

17. The composition of claim 16, in which $R_2$ is $C_{1-5}$alkyl.

18. The composition of claim 16, in which $R_2$ is H.

19. The composition of claim 18, in which $R_1$ is

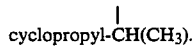
cyclopropyl-CH($CH_3$).

20. The composition of claim 18, in which $R_1$ is isopropyl.

21. The composition of claim 18, in which $R_1$ is cyclopropyl.

22. A method of combatting phytopathogenic fungi which comprises applying to the locus thereof a fungicidally acceptable effective amount of a compound of claim 1, in free form or in agriculturally acceptable acid addition salt, alcoholate or metal complex form.

23. The method of claim 22, in which the group R—C≡C— is in the para-position;
R is chlorine, bromine or phenyl optionally substituted by halogen, $C_{1-5}$alkyl, $C_{1-5}$alkoxy, $CF_3$, $OCF_3$, $NO_2$ or phenyl;
$R_1$ is i-$C_3H_7$, t-$C_4H_9$, $C_{3-6}$cycloalkyl or $C_{3-6}$cycloalkyl-$C_{1-3}$ alkylene;
X is hydrogen; and
Az is 1,2,4-triazol-1-yl.

24. The method of claim 23, in which R is phenyl.

25. The method of claim 24, in which $R_2$ is $C_{1-5}$alkyl.

26. The method of claim 24, in which $R_2$ is hydrogen.

27. The method of claim 26, in which $R_1$ is

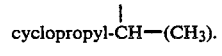
cyclopropyl-CH—($CH_3$).

28. The method of claim 26, in which $R_1$ is isopropyl.

29. The method of claim 26, in which $R_1$ is cyclopropyl.

* * * * *